United States Patent [19]
Seguin et al.

[11] Patent Number: 5,792,784
[45] Date of Patent: Aug. 11, 1998

[54] COUPLING PRODUCT OBTAINED FROM HISTAMINE AND AN AMINO ACID

[75] Inventors: Marie-Christine Seguin, Eze, France; Marc Babizhayev, Ivanovskaya 20, 74 Moscow 127434, U.S.S.R.

[73] Assignees: Marc Babizhayev, Moscow, U.S.S.R.; Exsymol Societe Anonyme Monegasque, Monaco

[21] Appl. No.: 507,266

[22] PCT Filed: Feb. 21, 1994

[86] PCT No.: PCT/FR94/00189

§ 371 Date: Aug. 21, 1995

§ 102(e) Date: Aug. 21, 1995

[87] PCT Pub. No.: WO94/19325

PCT Pub. Date: Sep. 1, 1994

[30] Foreign Application Priority Data

Feb. 22, 1993 [FR] France .................. 93 02295
Aug. 30, 1993 [FR] France .................. 93 10486

[51] Int. Cl.$^6$ .................. A61K 31/415; C07D 233/64
[52] U.S. Cl. .................. 514/400; 548/338.1; 548/338.5
[58] Field of Search .................. 548/338.1, 338.5; 514/400

[56] References Cited

U.S. PATENT DOCUMENTS

| | | | |
|---|---|---|---|
| 4,381,239 | 4/1983 | Chibata et al. | 210/679 |
| 5,002,963 | 3/1991 | DeLuca et al. | 514/419 |
| 5,132,400 | 7/1992 | Gammill et al. | 530/317 |

OTHER PUBLICATIONS

Gajda et al., J. Chem. Soc. Dalton Trans., 15, 2313–19, 1992.
Flancbaum et al., Life Sciences, 47, 1587–93, 1990.
Fesus et al., J. Biol. Chem., 260(25), 13771–8, Nov. 1985.

*Primary Examiner*—Rose G. Dees
*Assistant Examiner*—Laura R. Cross Lutz
*Attorney, Agent, or Firm*—Ostrolenk, Faber, Gerb & Soffen, LLP

[57] ABSTRACT

The invention relates to a pseudo-dipeptide product obtained by coupling between histamine or methyl-substituted histamine and an amino-acid having formula

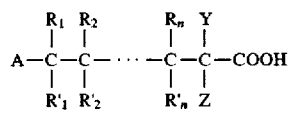

wherein A is a radical selected in the group comprising amine radicals, amides, lactames, urethans; $R_1$, $R'_1$, $R_2$, $R'_2$, ... $R_n$, $R'_n$ represent each a hydrogen atom, a hydrocarbon radical or a functional group; Y and Z represent each a hydrogen or a fluorine atom, or a hydrocarbon radical which may be substituted by one or a plurality of functional groups; and n is an integer higher than or equal to 1; the covalent bond with the histamine or the methyl-substituted histamine being a peptide bond between the carboxylic radical of the amino acid and the amine radical of the histamine. The pseudo-dipeptide products of the invention may be used in therapeutical, cosmetological and agro-alimentary applications and particularly for the treatment of cataracts.

28 Claims, No Drawings

COUPLING PRODUCT OBTAINED FROM HISTAMINE AND AN AMINO ACID

This application is a 371 of PCT/FR94/00189 filed Feb. 21, 1994.

BACKGROUND OF THE INVENTION

The present invention relates to histamine-derived products and more particularly to a coupling product between histamine or methyl substituted histamine and an amino-acid, its way of preparation and its applications as an active principle on the therapeutic and cosmetologic field or as an agent improving the stability of formulations in the therapeutic, cosmetologic or agro-alimentary field.

The biological characteristics of dipeptides such as β-alanyl-histidine are particularly interesting as far as they contribute to increase the natural ways of defense and repair of the organism. Nevertheless compounds including an amino-acid or more in their structure such as β-alanyl-histidine, form a range of active principles generally well tolerated by the organism but which efficiency is considerably reduced because these products are quickly degraded by the organism. Moreover, though the sensitivity to enzymatic desactivation is considerably reduced for the very small peptides (J.Dressman "Opportunities for peptide absorbtion in the GI tract", Communication GTRV 1992, Paris), the enzymatic desactivation of dipeptides could lead in some instances, to the liberation of histamine. This activity "pro-histamine" associated with the loss of activity of the original dipeptide, is not desired in the scope of this invention.

Therefore, the main object of this invention is to finalize peptide products close to the dipeptides mentioned above, but which efficiency is not reduced, owing to the fact they are not degraded by the organism.

Another object of the invention is to carry out a pseudo-peptide product derived from histamine having the characteristics of increasing the natural ways of defense and repair of the organism.

Still another object of the invention is to carry out a pseudo-peptide product as defined above, and which bio-availability is improved in acetylating the amino extremity.

Still another object of the invention is to carry out a peptide product having an acetylated group as defined above, so that hydrolysis by enzymes of the acetylpeptide hydrolase type permits sustaining the release in situ of an active product.

Other features and advantages of the present invention will become apparent from the following description of the invention which refers to the accompanying drawings.

The invention relates therefore to a pseudo-dipeptide product obtained by coupling between histamine or methyl-sustituted histamine and an amino-acid having as a formula:

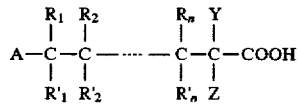

in which A represents a radical selected from the group consisting of amine, amide, lactam, and urethane radicals, $R_1, R'_1, R_2, R'_2, \ldots R_n, R'_n$ each represent an hydrogen atom or an hydrocarbon radical which can be substituted by one or several functional groups, Y and Z represent each an hydrogen or fluorine atom, or an hydrocarbonated radical that may be substituted by one or several functional groups, and n is an integer number superior or equal to 1, the covalent bond with histamine or methyl-substituted histamine being a peptide bond between the carboxylic radical of the amino-acid and the amine radical of the histamine.

Another object of the invention is a pseudo-dipeptide as defined in the previous object in which the oxygen atom of the carbonyl group obtained by coupling of the amino-acid and histamine is replaced by a sulphur atom.

Among the amino-acids corresponding to the formula of the invention, the following amino-acids give the best results:

β-alanine whose formula is:

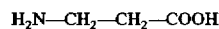
$H_2N-CH_2-CH_2-COOH$

τ-aminobutyric acid whose formula is

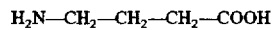
$H_2N-CH_2-CH_2-CH_2-COOH$

β-aminoisobutyric acid whose formula is

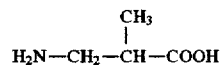
$$H_2N-CH_2-\underset{\underset{CH_3}{|}}{CH}-COOH$$

5-aminovaleric acid whose formula is

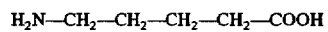
$H_2N-CH_2-CH_2-CH_2-CH_2-COOH$ 3-phenyl-3-aminopropionic acid whose formula is

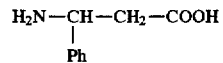
$$H_2N-\underset{\underset{Ph}{|}}{CH}-CH_2-COOH$$

6-aminocaproic acid

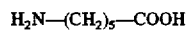
$H_2N-(CH_2)_5-COOH$ 8-aminooctanoic acid

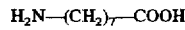
$H_2N-(CH_2)_7-COOH$ 4-methyl-aminobutyric acid

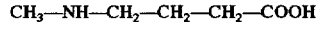
$CH_3-NH-CH_2-CH_2-CH_2-COOH$

DL-β-aminobutyric acid

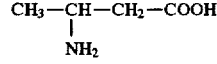
$$CH_3-\underset{\underset{NH_2}{|}}{CH}-CH_2-COOH$$

L-glutamic acid

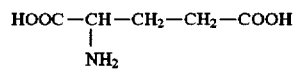
$$HOOC-\underset{\underset{NH_2}{|}}{CH}-CH_2-CH_2-COOH$$

The amino-acids in which we have acted to pyroglutamination of the radical $NH_2$

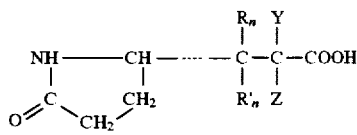

or the following amino-acids in which the amine extremity has been acetylated. As a matter of fact, the hydrolysis of this group with some enzymes (acetylpeptide hydrolase type) allows one to sustain the release in situ of an active product.

N-acetyl-β-alanine

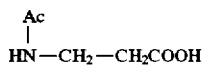

N-acetyl-3-phenyl-3-aminopropionic acid

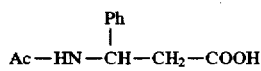

Besides the following acylated amino-acid possesses some inherent antioxidant characteristics that strengthen the activity of the pseudo-dipeptide product according to the invention

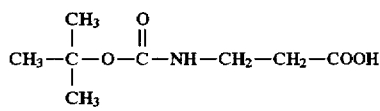

Nevertheless, β-alanine is the amino-acid which allows one to get a pseudo-dipeptide product perfectly carrying out the objectives of the invention. β-alanine can be coupled either with histamine whose formula is:

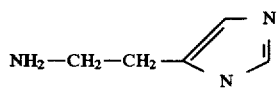

or with 1-methyl-histamine or 1-methyl-imidoazolethyl-amine

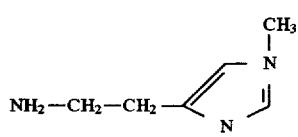

or with 3-methyl-histamine or 3-methyl-imidoazolethyl-amine

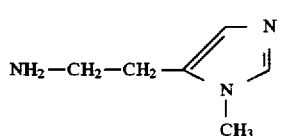

The pseudo-dipeptide product which is preferred in the scope of the invention is the β-alanyl-histamine whose formula is:

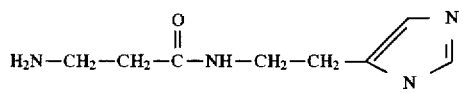

The preparation of the pseudo-dipeptide product according to the invention can be done either by using a chemical process or by using a synthesis method wholly or partly enzymatic.

The chemical preparation process presents itself according to the following diagram

 (1)

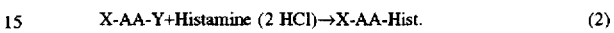 (2)

 (3)

The first step of the process consists in leading the amino-acid (AA) to be N-protected by an X coupling, and O-activated by an Y coupling.

N-protection is preferably carried out by the replacement of an hydrogen atom in the amino-acid amine through an X group which can be an acyl radical, acyloxy, etc. Among the most interesting protective group we can quote benzyloxycarbonyl, tertbutyloxy-carbonyl (BOC), 9-fluorenyl-methyl-oxycarbonyl (FMOC), the benzyl radicals, phthaloyl, 2-nitrophenyl-sulfenyl, trifluro-acetyl, with tertbutyl-oxycarbonyl being the one preferred.

Although it is possible to do without it, O activation is one of the characteristics of the process of obtaining a pseudo-dipeptide product according to the invention. This activation is carried out preferably by esterification of the amino-acid carboxylic acid function by a compound selected from the group consisting of: cyanomethyl alcohol, o-nitrophenol, 2,4,5-trichlorophenol, p-nitrophenol, 2,4-dinitrophenol, pentachlorophenol, pentafluorophenol, N-hydroxy-phtalimide, N-hydroxysuccinimide, 1-hydroxypiperidine and 5-chloro-8-hydroxy-quinoline.

So, if we use the pentafluorophenol as an Y coupling, the reaction is, if R—COOH is the amino-acid according to the invention

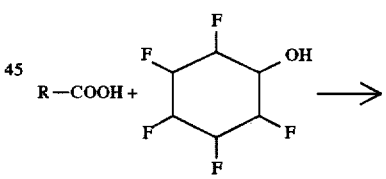

The second step of the process of preparation is the coupling with histamine which can be done with or without coupling agent, by getting the amino-acid N-protected and/ or O-activated to react to the histamine, preferably in a dihydrochloride form. We must quote that the coupling agent is not essential with an O-activated amino-acid.

The coupling without an agent of coupling is carried out in an organic solvent (for example chloroform, 1,2-dimethoxyethane, dimethylformamide, ...) together with an acid (for example acetic acid ...) or a base (for example triethylamine . . . ) in an hydro-organic solvent (for example pyridine-water or water-1,2-dimethoxyethane . . . ) together with a base (for example sodium hydroxide or sodium bicarbonate . . . ) then with an acid (for example hydrochloric acid . . . ); in some catalyts (for example imidazole, N-ethylmorpholine . . . ).

If we use a coupling agent, this agent can be for example the dicyclohexyl-carbodiimide, the 1-isobutyloxycarbonyl-2-isobutyloxy-1,2-dihydroquinoline, the carbonyldiimidazole, Woodward's reagent K, α-chlorovinyl ethyl ether, α,α-dichlorodiethyl ether, dichloromethyl methyl ether, DCC and additives, DCC-pentachlorophenol, DCC-pentafluorophenol, cyanamide, ketenimines and ketenes, oxazolium salts, EEDQ (1-ethoxy-carbonyl-2-ethoxy-1,2-dihydroquinoline), ynamines, acylphosphoniums, triphenylphosphite and imidazole, copper complex II, SiCl$_4$. . .

In the third step, the X coupling or N protective group is eliminated. This elimination is done, according to the protective groups, by hydrogenolysis, by sodium reduction in liquid ammonia, by hydrazinolysis, by acidolysis, by hydrolysis or by an enzymatic way. The preferred solution consists in carrying out this step of deprotection by acidolysis through hydrochloric acid in the acetic acid. In this last instance, the pseudo-dipeptide product is obtained under the form of hydrochloride, and it must be treated with some basic resin in order to recover the base product.

As an example, the preparation of β-alanyl-histamine can be done by using the following way:

370 mg of histamine hydrochloride (2 mmol) are dissolved in 7 ml of dimethylformamide (DMF). 0.56 ml of triethylamine (4 mmol) and 800 mg of N-tertbutyloxycarbonyl-β-alanyl-pentafluorophenyl-ester (2.25 mmol) are added to the mixture. The mixture is stirred up for 30 minutes at 0° C. then for 3 hours at room temperature. The residue is filtered then washed with dimethylformamide. Dimethylformamide is vacuum-evaporated. Ether is added to the residue and the resulting oily compound N-tert-butyloxycarbonyl-β-alanyl-histamine is recovered by decantation. Alanyl-histamine hydrochloride is then obtained by the treatment of N-tertbutyloxycarbonyl-β-alanyl-histamine with the hydrochloric acid dissolved in acetic acid for 30 minutes. The acetic acid is partially vacuum-evaporated and some ether is added again to the residue. The residue is then filtered. The recrystal-lization by the ethanol/methanol system (50/50)—ethyl ether leads to obtain 300 mg of β-alanyl-histamine hydrochloride. Finally, β-alanyl-histamine in its base form is obtained by elution of the hydrochoride form on a suitable resin.

The enzymatic synthesis method is done by using the following coupling reaction, once the amino-acid (AA) is N-protected (X group) and O-activated (Y group).

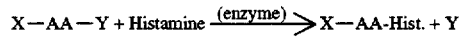

In this case, N-protection which preparation has already been described in the chemical preparation process allows also to increase the amino-acid solubility in the reaction medium. This allows choice of X coupling so as to increase the amino-acid solubility in the organic medium. Thus, X is preferably the benzyloxycarbonyl radical, X=Ph—CH$_2$—O—CO—.

O-activation can be done by esterification of the carboxylic acid radical through an alcohol selected from the group consisting of: aliphatic alcohol, preferably ethanol, halogeno-alkylalcohols such as 2,2,2,-trichloro-ethanol, the aromatic alcohols such as phenol, as well as alcohols already quoted for the chemical preparation process. Nevertherless, tertiary alcohols have to be left out.

The reaction of the coupling with histamine (or its methylated derivatives), or a salt of histamine (or its methylated derivatives), for example the dihydrochloride of histamine, is carried out in a variety of organic solvents such as aliphatic hydrocarbons (cyclohexane, heptane . . . ) or aromatics (toluene), tertiary alcohols (tert-butanol, tert-amylalcohol), alkyl halides (methylene chloride), ethers (isopropylether), acetonitrile, dimethylformamide or dimethylsulfoxide. Those solvents can be used either alone or mixed together; they can be anhydrous or contain a weak quantity of water.

The reaction can be conducted with or without a base, such as triethylamine.

The enzymatic catalyst is an hydrolase (lipase) of microbial, animal or vegetal origin. It can be in a pure or non-purified state.

Thus, we can take as a catalyst the lipases extracted from micro-organisms: pseudomonas Sp., candida Rugosa, Mucor, or of animal origin: pork pancreatic lipase (LPP), proteases: trypsin, chemotrypsin, substilisin, papain.

The catalyst, non-soluble in the reaction medium, is spread in the solvent alone or fixed on an inert support in order to make easier its recycling.

The reaction is carried out at a temperature between 4° C. and 70° C., but preferably between 35° C. and 45° C. under stirring.

The product of coupling is collected by filtration or after extraction with an appropriate solvent.

The deprotection and purification can be carried out according to the method described above in connection with the chemical preparation process. Nevertherless, this step of deprotection can be carried out by an enzymatic reaction according to the diagram:

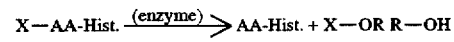

The procedure is similar to the one described for the coupling step. However, in the case where R=H the reaction is done in water.

For the coupling step, it can be less agreeable but allow reducing in an important way the costs of production, using either a non N-protected amino-acid (where X=H) but O-activated or an amino-acid N-protected, but non O-activated (where Y=H), or even the amino-acid (X=Y=H). The experimental conditions are similar to the ones previously described for the case where amino-acid is N-protected and O-activated.

In the following example, N-acetyl-β-alanyl-histamine is prepared as follows:

2.38 g (15 mmoles) of N-acetyl-β-alanine ethyl ester and 1.11 g (10 mmoles) of histamine dissolved in 40 ml of a mixture tert-amylalcohol-heptane (25:75)

0.5 g of lipase Amano P (pseudomonas Sp.) are added and the suspension is heated at 4° C., under the stirring for 48 hours.

The complete vanishing of histamine is verified by HPLC (R.P.C.-18-H$_2$O—CH$_3$CN—TFA:99/1/0.1).

The catalytst is then recovered by filtration. The organic solvent is vacuum-evaporated in order to give an oily compound. This residue is ground in ethyl ether in order to eliminate the excess of N-acetyl-β-alanyl ethyl ester. We obtain 1.9 g of N-acetyl-β-alanyl-histamine.

Pharmacological Properties

As it has already been mentioned, the pseudo-dipeptides products according to the invention can potentiate some mechanisms of defense and repair of the organism. They fight in that manner against ageing, and against degenerescence of the tissues (ocular, muscular, cutaneous . . . ), and they favour healing.

The anti-oxidant characteristics of these products, and more precisely their character as free radicals (FR) scavenger, and their ability to eliminate toxic peroxidation products for the organism, partly account for the pharmacological properties observed. The ability of these products to fight against the "oxidative-stress" and therefore to make up for the anti-oxidant defense systems of the organism, allow them to interfere in various pathologies. We can quote their anti-inflammatory action, their part in protection against radiation at the time of radiotherapy; their anti-atherosclerosis (inhibition of LDL oxidation); anti-cataract or anti-tumoral characteristics which are now described in the Scientific litterature.

As it has already been mentioned, the pseudo-dipeptides products according to the invention present characteristics anti-ageing, and anti-degenerescence of the cutaneous and mucuous tissues. In a general way, those characteristics are due to the anti-oxidative activity of these products and in particular to the anti-free radicals activities, pseudo-peroxidase, anti-reticulation, and regeneration of tissue that they demonstrate.

Moreover, multiple experimental analytic and epidemiologic arguments militate in favour of the therory according to which accumulation of biochemical damages caused by free radicals would constitute the essential ageing process. It is especially clear, that the exposure to sun radiation, responsible for the formation of free radicals species derived from oxygen, is a reason of the premature cutaneous ageing, as it is the main factor in the formation of the so-called senile cataract.

Most of the cellular constituents as a matter of fact represent potential targets for the attack of free radicals. The unsaturated fatty acids that are being part of the membrane phospholipids are particularly sensitive to their aggression. Their oxidation leads to the membrane disorganization, to the loss of intracellular components, to the (toxic) aldehydes formation and to lipoproteic complexes (lipofuscins). Proteins are also targets for free radicals, and their attack leads to the denaturing of proteins and to their being cut apart. The damage of the conjonctive tissue by the free radicals is an important part of their destructive action. The sugar-containing constituents are also attacked, the hyaluronic acid is depolymerized, and the glycoproteic membrane receptors are damaged. Finally, the nucleic acids are targets of a large functional extent.

Another characteristic of the pseudo-dipeptide products according to the invention accounting for the proteins protection in regard to the "oxidative-stress" is the presence of the imidazole ring of histamine. Indeed, the oxidative phenomenon, responsible for the proteins damage, seem to involve particularly the imidazole ring of the amino acid histidine (Ref."Hydroxyl radical mediated damage to proteins with special reference to the cristallins"—Biochemistry, vol.31 (1992), p.4296). It shows then that the compounds can play a part of "bait" for the free radicals.

The pseudo-dipeptide products according to the invention can resist at another level to the "oxidative stress". These compounds are capable of reacting not only on the free radicals species but downstream from the oxidative phenomenon, on toxic by-products, the peroxides, issued from the free radical reaction on some cell constituents. This acitivity called "peroxidase", by analogy with the name given to the enzymes in charge of eliminating in the organism the peroxides, allow one to neutralize those peroxides and then to prevent chain reactions, which in particular lead to the breaking of the cell membrane. That way we obtain a repairing activity.

Several in vitro tests have been carried out in order to reveal the evoked different antioxidant properties.

Experimental procedure described by J. M. C. Gutteridge in Biochemistry Journal, vol. 224 (1984), p. 761–767:

oxidation substrate: deoxyribose

Superoxide anions production system: xanthine oxidase/hypoxanthine detection: thiobarbituric acid/malondialdehyde (MDA)

|  | % inhibition |
| --- | --- |
| control | 0 |
| L-carnosine (10 mM) | 37 |
| β-alanyl-histamine (10 mM) | 49 |

This activity also has an action upon protection of the membrane phospholipids. Oxygen derived free radicals react with phospholipids, forming instable products which worsen and induce the breaking of the cell membrane.

The following tests illustrate this action.

PROCEDURE 1 oxidation substrate: phosphatidylcholine liposomes free radicals generating system : Fe/ascorbic acid detection: thiobarbituric acid (TBA)/malondialdehyde (MDA)

Protocol described in "Anti-oxidant activity of L-carnosine, a natural histidine-containing dipeptide in cristallin lens".

Biochem. Biophys. Acta (1989), vol 1004, p.363–371.

|  | mol MDA per mg of phospholipids | % inhibition |
| --- | --- | --- |
| Control (without inhibitor) | 4.4 | 0 |
| β-alanyl-histainine (10 mM) | 2.5 | 42 |
| 15L-carnosine (10 mM) | 2.0 | 53 |
| Histamine (10 M) | 6.8 | −63 |
| Histainine 1 M | 6.4 | −45 |
| Histidine 1 mM | 6.6 | −48 |

PROCEDURE 2 oxidation substrate: linoleic acid (0.25 mg/ml), free radicals generating system: Fe/ascorbic acid detection: thiobarbituric acid (TBA)/malondialdehyde (MDA)

|  | mol MDA per. mg of linoleic acid | % inhibition |
| --- | --- | --- |
| Control (without inhibitor) | 7.95 | 0 |
| β-alanyl-histamine (25 mM) | 4.25 | 47 |
| L-carnosine (25 mM) | 3.24 | 59 |
| Imidazole (25 mM) | 6.95 | 11 |
| β-alanine (25 mM) | 7.91 | 0 |
| Histamine (25 mM) | 10.15 | −32 |
| β-alanine (25 mM) |  |  |

| | mol MDA per. mg of linoleic acid | % inhibition |
|---|---|---|
| +histamine (25mM) | 9.06 | −15 |

The peroxidase type activity of pseudo-dipeptides products of the invention proceeds through the reduction of the peroxide type L-OOH resulting from the membrane lipids attack by oxygen-derived free radicals. Those peroxidated forms can break up, involving the breaking of the cell membrane. This mechanism of action is complementary to the anti-free radical activity, allowing an especially effective desactivation of the degradation proceeding of the biological membranes. This reaction is called "peroxidase activity", by analogy with some enzymes (catalases, glutathione-peroxidase) which act on the hydrogen peroxide.

A pseudo-dipeptide product according to the invention such as β-alanyl-histamine inhibits the reaction L-OOH→products of degradation (tetradienes, cetodienes), by reducing the peroxide

L-OOH→L-OH

Some tests carried out with peroxidized compounds such as 13-monoperoxide of linoleic acid or the hydroperoxides of phosphatidylcholine show that a pseudo-dipeptide product according to the invention, β-alanyl-histamine behaves in a way comparable to β-alanyl-histidine or carnosine. The biological reducing behaviour of this product has been compared to a chemical reducing agent, sodium borohydride, which inhibits in an identical way the reaction of degradation.

The following tests illustrate this activity

PROCEDURE 1

Lipid peroxides evolution is monitored with the help of 3 methods:

1°) spectrophotometric measure at 233 nm
$e = 2.8 \cdot 10^4 M^{-1} cm^{-1}$
(O. S. Privett, C. Nickell, W. O. Lundberg, and P. D. Bayer, dans J.Am.Oil Chem. Soc. Vol 32 (1955), P.505–511

2°) Iodometric dosage: M.Hicks' and J. M. Gebicki's method, Analytical Biochemistry, vol 99 (1979), p 249–253.

3°) Chromatography on silica gel plate (hexane/ether/acetic acid 8/7/0.1).

| | "peroxidase" activity mol of L-OOH reduced/hour | |
|---|---|---|
| Control (a) | 36.7 | 14.7 |
| β-alanyl-histamine (10 mM) (b) | 138.1 | 18.7 |
| β-alanyl-histamine (20 mM) (b) | 187.5 | 15.7 |
| NaBH$_4$ (10 mM) (c) | 312.5 | 14.5 |

(a) 13-monoperoxide linoleic acid 0.5 mM without reducing agent (preparation according to H. W. Gardner's method Lipids, Vol. 10 (1975), p. 248–252).

b) actitvity completely inhibited with the adding of EDTA 0.5 mM (c) chemical reducing agent

PROCEDURE 2

The "peroxidase" type activity also has been evaluated on a "liposome" model. The phosphatidylcholine hydroperoxides (PC-OOH) are prepared according to a similar procedure to the one already described for the linoleic acid monoperoxide.

The peroxide species reduction is followed by dosing the remaining peroxides according to the method laid down by Hicks M and Gebicki J. M.—Anal. Biochem, vol 99, (1979), p. 249–253.

| | number of moles of PC-OOH reduced/initial number of moles of PC/hour |
|---|---|
| β-alanyl-histamine (10 mM) | $0.77 \times 10^{-3}$ |
| L-carnosine (10 mM) | $3.16 \times 10^{-3}$ |
| β-alanyl-histamine (25 mM) | $1.56 \times 10^{-3}$ |
| L-carnosine (25 mM) | $3.65 \times 10^{-3}$ |

Reading the above tests, we notice that in some cases, L-carnosine gives better results than β-alanyl-histamine. Meanwhile, the enzymatic desactivation of the L-carnosine at the cutaneous level does not allow one to hope as good results in-vivo.

The pseudo-dipeptides according to the invention can react more downstream from the "oxidative stress" phenomenon by their "anti-lipofuscins" effect. We have already seen it, peroxidation of fatty acids, and in particular phospholipids, lead to their breaking. Those by-products of fragmentation are toxic, and they provoke the proteins reticulation. The pigmented lipoproteic complexes that are created are called "lipofuscins".

Fatty acid peroxidation by free radicals does not only destroy these acids but also inactivates the proteins with "cross-linked polymers" formation. This process, which is done to the prejudice of the enzymes and at the same time the cellular organoids, is considered to play a part in the ageing process. Those polymers derived from a cross linking between polyunsaturated fatty acids and proteins are called lipofuscins.

The pseudo-dipeptides of the invention reinforce the natural defenses of the organism, allowing limitation of the proteins deterioration through this process significantly by reducing the lipoproteic complexes formation.

Another way of action for those pseudo-dipeptide products according to the invention is based on their anti-glycation properties, that is to say their ability to inhibit the spontaneous condensation between the amino moieties of the proteins and reducing sugars, and mainly glucose.

The sequence of successive chemical reactions that follows was known for the last ten years by chemists in food processing under the name of Maillard's reaction. It induces an accumulation of non-reversible links between proteins, which numbers increase with the age. It creates "cross-links" between proteins such as collagen or elastin (Ref. K. Reiser, R. J. Mc Cormick, and R. B. Rucker—"Enzymatic and nonenzymatic cross-linking of collagen and elastin"—FASEB Journal, vol. 6 (1992), p. 2439–3449), the result of which is a stiffening and a "rigidification" of the tissues, characteristic phenomenons of the ageing tissues. This phenomenon above all concerns the proteins having a long duration time of life (proteins of lens, collagen, myelin). It is also responsible for the "cataract of diabetics", the formation of reticulated proteins is strongly accelerated among this type of people.

The antiglycation is due to the fact that pseudo-dipeptides products according to the invention are aminated nucleophilic compounds which set themselves against proteins sugar-mediated reticulation, interfering at the level of intermediates of Maillard's reaction (see above). In the products of the invention, it is a nucleophilic amine sterically not very hindered which confers this property.

Finally, the activity of cell regeneration in the healing process has been demonstrated for the pseudo-dipeptides products according to the invention. As a matter of fact, the healing process is made up of three phases: a vascular and inflammatory phase, a proliferative phase where fibroblast proliferation and neosynthesis of collagen occurs, and a phase of remodelling during which is reached an equilibrium between collagenolysis and biosynthesis.

In this process, the pseudo-dipeptides products act as chemiotactics or activators which provoke the coming towards the cicatricial site of cells participating to the remaking up of the tissues.

A test demonstrating the activity of the pseudo-dipeptide product according to the invention, β-alanyl-histamine, on the repairing of the cutaneous connective tissue has been performed on rat. This experiment has been carried out on a batch of 12 Wistar rats. An incision of a length of 12 mm involving in depth epiderm and derm as a whole was performed. At the end of the healing, the rats are then treated by topical applications of β-alanyl-histadine for three weeks. At the same time, a reference batch of 12 rats have been treated with placebo for the same lasting time of experiment.

After the 3 weeks of experiment, a histological sampling of the cicatricial tissue has shown that the scar is slightly or even not visible on the skin surface. The epiderm is well restored. The horny-layers are identical to the ones of the surrounding normal epiderm. They show a variable aspect depending on whether we consider the reference animals or the treated animals.

The dermic zone on the way to healing appears like a relatively narrow strip spreading out from the epiderm to the muscular layer. The limit of the non-injured zone is clean, without any aspect of transition. The density and the aspect of the constituents of the connective tissue are obviously the same in the capillary layer and in the deep layer. Meanwhile, the thin elastic or reticulin fibres are generally more numerous in the dermic superficial layers. The fundamental substance is more abundant than normal as it is shown by the colouring with toluidine blue (metachromasis at acidic pH and Lissberg's technique).

On the other hand, the rats from the reference batch present an epiderm with a cicatricial swelling with a thickness superior to the normal. We note a fibroblastic and neovacular hyperplasia on the whole of the cicatricial zone. Besides, the fibroblasts are temperately hypertrophied. Some rare thick collagen bundles can be observed, but the major part of the bundles are short and of an average thickness.

According to the other way of action, the pseudo-dipeptides products according to the invention would favour the healing by acting on the cells of the immune system involved at an early stage in the healing (lymphocytes, mastocytes, monocytes) and which main role is the secretion of growth factors.

This immunostimulating activity is revealed thanks to a test in vitro on murine splenocytes. The procedure is extracted from: J. Kunert-Radek, H. Stepien, K. Lyson and M. Pawlikowski—"Effects of calcium channel modulators on the proliferation of mouse spleen lymphocytes in vitro"—Agents and Actions, vol. 29, Nos 3–4 (1990), p. 254–258.

The cell proliferation is followed by the measurement of the extent of incorporation of tritriated thymidine in the cells, expressed in numbers of desintegrations per mn, deducted from the background.

The results obtained with an immunostimulator of reference, concanavaline A, are given as a comparison.

The immunostimulating effect is expressed by an Index of Stimulation (IS)

$$IS = \frac{\text{Nb of desintegrations by mn of a cell suspension added with a mitogen compound}}{\text{Nb of desintegrations by mn of a cell suspension of reference without mitogen}}$$

The given values are corresponding to the average of three measures.

As a matter of fact, we observe a maximum immunostimulating effect for a β-alanyl histamine concentration of 25 µg/ml. In short, we observe a reasonable immunostimulating effect (cell proliferation) for this pseudo-dipeptide for concentrations included between 5 and 25 µg/ml.

|  | concentration of immunomodulator µg/ml | | | | |
|---|---|---|---|---|---|
|  | 2.5 | 5 | 10 | 25 | 50 |
| IS (β-alanyl-histamine) | 4.8 | 15.7 | 16.9 | 18.6 | 12.8 |
| IS (concavanaline A) | 4.8 | 25.1 | 20.5 | 12.6 |  |

This activity is comparable with a reference mitogen, concanavaline A.

The pseudo-dipeptide products according to the invention can participate to the protection of the organism against the allergic reactions, and especially by blocking the anaphylactic shock, in demonstrating a regulative activity of the immune response.

This type of product could also restrict the permeability of the blood vessels, responsible of the edema, and by an antagonistic effect towards bradykinine, an effector to the edema formation (Ref. K. Nagai Ed.—"Studies of carnosine and related chemicals on the physiology of wound repair mechanism", pages 24–26, Tokyo (1976). It is the potential anti-histamine character of this family which would play a role in this property.

Therapeutic and cosmetologic applications

The properties on the whole stated above, whose essential characteristic is to participate in the reinforcement of the natural ways of defense and repair of the organism lead to appreciable therapeutic and cosmetologic applications for the pseudo-dipeptides according to the invention.

The antioxidant properties of the pseudo-dipeptides according to the invention allow these products for pathology treatment due to the "oxidative stress".

An important therapeutic application is the cataract treatment. The reasons for the different cataracts are various. The mechanisms involved in those pathologies, whether they are "senile cataract" type or "diabetic cataract" type, are gathered in two categories: the mechanisms of oxidation (M. A.Babizhayev, A. I. Deyev, L. F. Lindberg, "lipid peroxidation as a possible cause of cataract", Mechanisms of Ageing Dev., Vol 44 (1988); p. 69–89), and the mechanism of the glycation type reticulation (T. J. Lyons, G. Silvestri, J. A. Dunn; D. G. Dyer, J. W. Baynes "Role of glycation of lens cystalins in diabetic and non diabetic senile cataracts", Diabetes Vol. 40, N°. 8 (1991), p.1010–1015).

As seen previously, the antioxidant properties of the pseudo-dipeptides experiencing in particular in their anti-free radicals activity and "peroxidase" type and also in their anti-glycation activity, make the pseudo-dipeptides products according to the invention efficient products to treat cataracts.

The pseudo-dipeptides according to the invention can resist to the oxidative phenomenons responsible for the atherosclerosis. In this pathology, the oxidation of lipoproteic particles with a low density (LDL) flowing in the blood stream is responsible for the fragmentation of the proteic part (apoprotein B) as it is for the lipidic fraction of those particles. The fragments formed would induce the coming out of abnormal cell kinds (monocytes and macrophages loaded in cholesterol) capable of aggregating on the walls of the blood vessels and of forming the atheromatous plaque.

The pseudo-dipeptides products according to the invention moreover would be, especially adapted to the treatment of this disease as far as it has recently been demonstrated that the glycation phenomenoms are also involved in the genesis of the atheromatous plaque (Ref. T. J. Lyons—"Glycation and oxidation—A role in the pathogenesis of Atherosclerosis"—American Journal of Cardiology, vol. 71, N°.6 (1993), p. 1326–1331).

The pseudo-dipeptide products according to the invention can also resist the process of cancerogenesis insofar as it has been demonstrated that the radicals species derived from oxygen are responsible for the cutting or the change of DNA strands, these transformations being able to be the beginning of the evolution for healthy cells to become tumoral cells.

In the same way, antioxidant properties of pseudo-dipeptides products according to the invention allow the indication of these products for the treatment of pathological inflammatory state, and in particular for the treatment of rhumatoid arthritis. As a matter of fact, the deterioration of the synovial liquid is a characteristic symptom of the inflammatory type arthritis and it was shown that the degradation of one of its essential constituents, hyaluronic acid, was due to an "oxidative stress". More recent studies (Ref. B. Halliwell and J. M. C. Gutteridge "chronic inflammation and the autoimmune disease"—Free radicals in Biology and Medecine—B. Halliwell and J. M. C. Gutteridge Eds—Clarenton Press (1989), Oxford, p. 422–438) have also implicated lipids peroxidation phenomenons involved in this process and which would explain the beneficial action of the products according to the invention.

The antioxidant properties of the pseudo-dipeptides products according to the invention can also be used as a supplement in radiotherapy. This radioprotective effect, already known for β-alanyl-histidine, lean on cystostimulating properties of this type of compound, especially with regard to the bone marrow cells, very sensitive to radiations used in radiotherapy.

According to recent data, some epileptic symptoms could result from produced lesion by the oxygen derived free radicals on certain zones of the brain (Ref. G. R. Jackson, K. Werrbach-Perer, J. R. Perez-Polo—"Role of nerve growth factor in oxidant-antioxidant balance and neuronal injury—II—A conditioning lesion paradigon"—Journal of Neuroscience Research, vol.25, N°.3 (1990) p. 369–374). The regenerative ability on the tissues (nervous in this case) of the products of the invention is an important element in the pathology connected with a degeneration of the nervous tissue. These products could also be indicated for the treatment of Parkinson's disease in which would be involved an "oxidative stress" concerning the brain tissue.

At the skin level, the anti-oxidant properties of the pseudo-dipeptides products of the invention can be exploited to neutralize the effects of the oxygen derived free radicals species generated by the sunlight. That way they will efficiently block the photoallergic reactions (free radicals species induce at the skin level the formation of photo sensitizing molecules). In connection with a sensitive active principle to oxidation (eg: chlorpromazine), they will prevent its transformation into a toxic compound.

This principle finds its best application during the treatments by photochemiotherapy of certain skin diseases. Indeed, these treatments lean on the use of a photosensitizer (eg: psoralen), which under radiation brings a benefic action (interaction with DNA) but which, unfortunately is connected with the formation of radical species responsible for undesirable secondary effects.

The products of the invention can also be indicated in order to resist to the effects of cutaneous symptoms in people with porphyrias, because the porphyrins potentiate the damages due to free radicals.

They will also set themselves against the formation of cutaneous lesions linked to the "oxidative stress" in people suffering of autoimmune disease such as Systemic Lupus Erythematosus (SLE).

Also they will efficiently set themselves against effects of "sun burns": erythema, edema and formation of sunburn cells in the skin.

The antioxidant properties of the compounds according to the invention can of course be used for the prevention of the cutaneous ageing. The theoretical and experimental arguments which justify this approach previously have been given.

Finally it has been demonstrated that these compounds fight against other distinctive phenomenons of the cutaneous ageing tissue.

The nonenzymatic reticulation of proteins such as collagen or elastin mediated by sugars (V. M. Monnier—"Nonenzymatic glycosylation, the Maillard reaction and the aging process"—Journal of Gerontology, vol. 45, N°. 4 (1990), p. B105–111).

The formation of lipoproteic complexes (lipofuscins).

Another range of applications are dependent on cytostimulating properties of the pseudo-dipeptides products according to the invention and, as it has been demonstrated, on their immunostimulative properties. These properties allow favouring tissue regeneration and healing, and in a general manner to regulate the functions that implicate the mediators of the immune response.

That way they can be used to favour the disturbed cutaneous connective tissue regeneration. They favour the repair of mucosa afterburns or after chemio or radio therapies.

According to this principle, these products can also be indicated for the prevention and wrinkles treatment.

The cytostimulative and regenerative properties of the pseudo-peptides act with a particular attention towards the muscular tissues where we can meet high concentrations of a related natural dipeptide, the β-alanyl-histidine. Although the physiological role of this compound is not, at the present time, perfectly established, it is closely linked to the muscular metabolism. So, the products of the invention could participate to the improvement of the muscles contractility, and regulate the heart contractions. We can use also this type of properties for the treatment of certain muscular degeneration as the Dushen's myodystrophy.

The healing properties of the pseudo-dipeptide products, according to the invention find their application in numerous fields. We can quote the treatment of gastric ulcer for which a dipeptide product related to carnosine has given good results (M.Ito, T. Tanaka and Y. Suzuki—"Effect of N-(3-aminopropionyl)—L-histidinato zinc (Z-103) on healing and hydrocortisone-induced release of acetic acid ulcers in rats with limited food-intake-time"—Japanese Journal of Pharmacology, vol.54 (1990), p. 513–521). Besides, the antioxidant and anti-inflammatory properties of the products of the invention are useful for this pathology treatment.

The healing properties of the pseudo-dipeptides products according to the invention also are particularly indicated for the treatment of the corneal impairs. They could be given in postoperative treatment after for example an incision of the cornea for the correction of myopia.

Also they can to the best advantage be used for the pathologies treatment of the "dry eye" favouring the healing of the corneal epithelium but also thanks to a behaviour of "artificial tears": protection of the injured tissues against the "oxidative stress" (state of health, inflammation, U. V. radiation), incorporation in the formulas helping the re-making of the tear film.

Compositions containing pseudo-dipeptides of the invention could also, by their immunostimulating and regenerative action, resist to the phenomenoms of the retina degeneration. They will see their effects reinforced owing to the fact that a component "oxidative stress" interferes in this pathology.(Ref. R. E. Anderson, L. M. Rapp, R. D. Wiegand—Current Eye Research, vol. 3 (1984), p.223–237).

Another important application of the pseudo-dipeptide products of the invention is more specifically in relation to their immunomodulation properties. So it could be particularly favourable to include pseudo-dipeptide products according to the invention in perfumes and deodorants in order to block the allergic reactions, and in particular to the anaphylactic shock provoked by some strong smelling composition.

Applications as stabilizer and preservative

The excellent tolerance towards pseudo-dipeptides according to the invention, and their moderated antioxidant and cytostimulative properties allow one to propose those products for the preservation and the protection of substances sensitive to oxidation, of food processing or organs and tissues preserved ex vivo.

We can quote the oxidation prevention of liposomes in order to improve their stability and to avoid the formation of toxic by-products, the protection of hyaluronic acid incorporated in cosmetic formulas against the depolymerizing action of free radicals, the protection of oils and oxidizable food products, and diet products.

The products of the invention allow one to improve the blood and serum vaccine, and preservation of organs dedicated to transplant (with a special reference for the heart).

The applications of the pseudo-dipeptide products of the invention have been revealed in the following examples which give the doses and the compositions of products used as medicine or as stabilizer agents.

EXAMPLE 1

This example concerns the utilization of the β-alanyl-histamine to treat patients affected by cataract.

The study has been designed for a prospective evaluation of the modifications of the lens opacity in patients effected by cataract. All the patients have undergone an initial ophtalmic examination. It involved the making of the medical historical record of the patient, a measurement of the visual acuity at a maximum correction, direct or indirect ophtalmoscopies, an evaluation of the opacities with the slit lamp, a clinical grading of the lens after maximal mydriasis, a classification according to the cataract type, and lens pictures by retroillumination. Moreover, samples of blood have been taken at the beginning, then in follow-up for chemical analysis.

The general view has allowed to establish the initial state of patients before the treatment (definition of "base line").

Follow-up of ophtalmic examinations were carried out every two weeks for two months, then every month. They included maximum visual acuity after correction, direct or indirect ophtalmoscopies, a slit lamp examination, and after a maximum dilation of the pupil (excluding patients with primary open-angle glaucoma), a clinical lens grading, a classification of the cataract. Pictures also have been taken on lens observed by retroillumination or with the slit lamp.

Changes of the lens have been examined in all the patients by using the microscope with the Zeiss slit lamp. The photographic observations obtained with this technique included a base line examination, intermediate studies and a final examination at the end of the treatment period.

In using the technique of the slit lamp, the lens has been pictured layer by layer in order to visualize all the anterior segment of the eye, from the cornea to the posterior capsule.

With this technique, Red reflex examination has been carried out, according to a conventional retroillumination. Then lens modifications were graded according to the anatomical location and the importance of the modification.

Cortical opacities have been graded and pictured in retroillumination. Afterwards this film has been submitted to a measurement of linear densitometry with a microdensitometer. The opacity values have been reported in relative value using a standard scale of opacification. The cortical opacities measurement have been rated also taking into account of the total surface exposed to radiation. The posterior subcapsular opacities have been measured in retroillumination by the longest height, from the lower part to the top and by the greatest width, using the scale of the slit lamp.

Pictures of the lens also were taken on nuclear and cortical opacities and later on they were graded.

The different negatives taken with the slit lamp have been analyzed with a "plumbicon tube". This equipment allows one to transpose with a large accuracy a measurement of intensity of light into an electric signal which is integrated and stored in an analysis system of computerized image. With the help of a specific program, the lens image in that manner "digitized" could be reproduced as a graph in two or three dimensions.

A detailed description of this method of image processing is given in : Babizhayev M. A. Zhukotskii A. V. and Sologub A. A. (1992), "Image analysis of the lens opacities induced in developing chick embryo by glucocorticoid", Exp. Eye Res. Vol. 55, p.521–537.

Examples of these reconstituted images are given in FIGS. 1A and 1B. The represented histograms show in a concrete example the interest of such evaluation method. A case of posterior subcapsular cataract is studied before and after 2½ months of treatment following topical applications with eye drops containing 1% of β-alanyl-histamine. The histograms give the quantitative distribution of opacities with an integration peak of 58.44±18.14 before treatment, and of 44.95±8.77 after 2½ months of treatment.

These analysis show a partial regression of the opacities in the posterior subcapsular region of the lens.

The results obtained with this method fit in with the standard clinical examinations.

In this study, differents groups have been determined, to be seen:

A group reference 1, with non-treated patients (5 patients, 7 eyes)

A group 2, to which an eye drop has been given which was an isotonic saline containing 1% of β-alanyl-histamine at pH 7.4, 2 local applications per day (10 patients, 15 eyes), A group 3, has been submitted to the same treatment than the group 2, stimulated by an "attack type of treatment" during the first two weeks: 2 subcon-junctival junctival injections twice a week of 0.10 to 0.15 ml of the saline defined for the group 2 (3 patients, 4 eyes).

A group 4, which was given a local dose by way of an eye drop of isotonic saline twice a day (5 patients 7 eyes), the group 4 being like the group 1, a reference group.

Following the protocol described above, we determine the values of the optic density of the lens according to its opacity as well as the visual acuity, and the whole for 24 months. Considering these two parameters, we obtain tables giving results concerning the modification of the visual acuity at the end of 24 months in Tables 1 and 2, and the results concerning the modification of the visual opacity at the end of 24 months in Tables 3 and 4.

TABLE 1

MODIFICATION OF THE VISUAL ACUITY AT THE END OF 24 MONTHS
Non-treated patients and treated with placebo (groups 1 and 4)

| start visual accuity | number of eyes | improvement of the visual accuity | | | stationary state | regression of the visual accuity | | |
|---|---|---|---|---|---|---|---|---|
| | | + | ++ | +++ | | + | ++ | +++ |
| 20/25 | 2 | — | — | — | | — | 2 | — |
| 20/30 | 1 | 1 | — | 0 | | — | — | — |
| 20/40 | 3 | — | — | — | | 1 | 1 | 1 |
| 20/50 | 1 | — | — | 0 | | — | — | 1 |
| 20/60 | 2 | — | — | — | | 1 | — | 1 |
| 20/70 | 1 | — | — | 0 | | — | 1 | — |
| 20/100 | 0 | — | — | — | | — | — | — |
| 20/200 | 3 | 1 | — | — | | — | — | 1 |
| <20/200 | 1 | — | — | — | | — | — | 1 |
| | 14 | 2 | 0 | 0 | | 2 | 5 | 5 |

TABLE 2

Treated patients (groups 2 and 3)

| start visual accuity | number of eyes | improvement of the visual accuity | | | stationary state | regression of the visual accuity | | |
|---|---|---|---|---|---|---|---|---|
| | | + | ++ | +++ | | + | ++ | +++ |
| 20/25 | 1 | 1 | — | — | | — | — | — |
| 20/30 | 5 | 1 | 4 | — | | — | — | — |
| 20/40 | 4 | 1 | 3 | — | | — | — | — |
| 20/50 | 2 | 1 | 1 | — | | — | — | — |
| 20/60 | — | — | — | — | | — | — | — |
| 20/70 | 2 | 1 | 1 | — | | — | — | — |
| 20/100 | 4 | — | 1 | 2 | | — | 1 | — |
| 20/200 | 1 | — | 1 | — | | — | — | — |
| <20/200 | 0 | — | — | — | | — | — | — |
| | 19 | 5 | 11 | 2 | | 0 | 1 | 0 |

TABLE 3

Non-treated patients and treated with placebo (groups 1 and 4)

| % of MODIFICATION | decrease of the OPACITY | stationary state | increase of the OPACITY |
|---|---|---|---|
| 5 @ 9% | — | — | 8 |
| 10 @ 14% | — | — | 2 |
| 15 @ 19% | 1 | — | 2 |
| 20 @ 24% | — | — | 0 |
| +25% | — | — | 1 |

TABLE 3-continued

Non-treated patients and treated with placebo (groups 1 and 4)

| % of MODIFICATION | decrease of the OPACITY | stationary state | increase of the OPACITY |
|---|---|---|---|
| | 1 | — | 13 |

TABLE 4

Treated patients (groups 2 and 3)

| % of MODIFICATION | decrease of the OPACITY | stationary state | increase of the OPACITY |
|---|---|---|---|
| 5 @ 9% | 3 | — | — |
| 10 @ 14% | 5 | — | — |
| 15 @ 19% | 5 | — | — |
| 20 @ 24% | 1 | — | — |
| +25% | 5 | — | — |
| | 19 | — | — |

It can be concluded that considering the two selected parameters, the given product is very significant in the improvement of the vision and the regression of cataract.

In the same way, we have experimented a kind of eye drop based on the active ingredient N-acetyl-β-alanyl-histamine on the basis of 1% in an isotonic saline which gives results corresponding to the objective of the invention. With only one daily local given dose, the results have been identical to the ones previously obtained. This established fact can be explained by a better biodisponibility of the acetylated form.

Although the above example states an eye drop, we can give the product according to the invention in the form of all ocular formulations generally accepted such as a gel or other (see ref. "Remington's parmaceutical sciences handbook" Hack Pub. Co. USA) containing 1 to 100 mM of β-alanyl-histamine.

EXAMPLE 2

It has been demonstrated the repairing activity on the mucosa of products according to the invention by using formulations at very weak doses. We have been able to study this action on stomatitis gingivitis of various origin (dental prothesis badly adapted, the taking by mistake of a corrosive liquid, and colbaltotherapy of the oropharyngeal aera.

In all the cases, the causes of deterioration of the gingival and buccal mucosa have been stopped. Over and above the classical treatments that were adapted and systematically given, was given to 50% of the patients, an aqueous orange flavour gel containing 0.28% of N-acetyl-3-phenyl-3-aminopropionyl-histamine.

The observations made on these different cases have demonstrated an excellent tolerance and a significant reduction of the repairing time going from 20 to 55%.

We can conclude to a positive activity having regard for the dose of formulation.

EXAMPLE 3

We have been able to demonstrate the healing properties by using a healing cream with the following composition:
Nanospheres (diameter 100 nm) containing
    5% of β-amino butyryl-histamine . . . 10 g
    Excipient hydrodispersible qs . . . 100 g
    pH 6.5

This cream has been applied twice a day in light massages on closed wounds. The cicatricial and approaching cicatricial zones have been massaged until complete penetration of the ointment.

The studied cases were three post-surgical scars of less than 14 month old, two with cheloids and five with after-effects suffering from acne.

In all the cases, it has been observed a significant improvement of the scar, a reduction of the swelling and irregularity of the skin until complete disappearance in two cases.

At the same time, it has been noted a reappearance of an uniform complexion with disappearing of the turgescences. These results are significantly positive.

EXAMPLE 4

The following eye drop has been used for the cornea injuries treatment and in particular on the pathology of the "dry eye".

liposomes made of phosphatidyl-choline . . . 8 mg/ml
Fibronectin of human plasma origin . . . 10 mg/ml
β-alanyl-histamine . . . 25 mg/ml in a buffered medium with pH between 6.2 and 7.4

The "fibronectin" and the β-alanyl-histamine are encapsulated in the liposomes.

The fibronectin is a cell attachment-molecule which is going to favour the healing and the reestablishment of the lachrymal film.

The eye drop is applied to the surface of the eye during 10 days on the basis of two instillations per day. The quantity applied must be sufficient in order to form a continuous film on the eye surface.

Results

The formula durably reconstitutes a protective layer on the eye surface, as it has been demonstrated by a study of retention on the cornea of an fluorescent tracer (procedure extracted from: R. F. Barber, P. N. Shek "liposomes and tear film .1. Release of vesicle entrapped carboxyfluorescein"— Biochimica Biophysica Acta: lipids and lipid metabolism, vol 879 (L81), n°.2 (1986), p. 157–163).

The healing is followed with the help of a slit lamp: we observe a rapid reconstitution of the corneal epithelium.

EXAMPLE 5

The ointment used in this example also has been used for the first and second degree superficial burns treatment.

parahydroxycinnamic acid . . . 0.1 g
mint oil . . . 0.3 g
lavender oil . . . 0.5 g
nanospherized menthol . . . 0.05 g
β-aminoisobutyryl-histamine . . . 0.5 g
excipient hydrodispersible qs . . . 100 g We apply the ointment in thin layer, as early as the appearance of the burn. The first time the application is repeated every hour, until the pain ceasing. On first degree burns, the erythema quickly disappears. On the superficial burns of second degree with flyctene and edema on reddened epidermis according to the burned surface, we observe a resorption of the edema within 2 hours, and a pain regression within 3 or 4 hours.

In the two or three days that follow, the tissues underneath are more rapidly regenerated. It is possible to release the vesicles of the liquid hold back by these latters with the formation of a new epidermic layer and elimination of dead tissues. On one hand, we note an acceleration of the epidermic repairing, on the other hand an excellent quality.

EXAMPLE 6

The anti-free radical activity of the pseudo-dipeptides products of the invention has been demonstrated in the following example of cosmetic formulation usable as an after-shave lotion.

6-aminocaproyl-histamine nanospherized at 5% . . . 16 g
liquid fragance excipient
hydroalcoholic 6° qs . . . 100 g A regular after shave application allows to preserve a skin in a good state.

EXAMPLE 7

Taking as a basis the same activity than the above example, a sun lotion has been carried out with the following formulation:

3-phenyl-3-aminopropionyl-histamine . . . 1 g
hydrolipidic excipient microdisperse qs . . . 100 g Different cases have been studied in the beauties salon at the time of UVB radiation courses. For equivalent tans, when we apply the cream after exposure, the epidermis presents a better quality in the following days of the radiation.

EXAMPLE 8

Always based on the same activity, we have carried out a cream for a good care of the face with the following composition.

solution of 5-aminovaleryl-histamine
nanospherized at 4% . . . 20 g
ions Cu ++, Fe++ (under the form acetylmethionine)
excipient hydrodispersible qs . . . 100 g
pH 6.5

For an anti-ageing cream, with two daily applications, we have noted a regression of the small wrinkles, a more lissom and more coloured skin.

For a cream being a good repairing care against various aggressions, a daily application is enough. We apply the cream by massages until complete absorption, the nanospheres are going to form an homogenous film with a long-lasting release. It is possible to apply make-up after the application of this cream.

We observe on the skin of the face, some visible results as demonstrated by the following criteria of good health, flexibility, freshness of the complexion, uniform colour and good hydration.

EXAMPLE 9

The pseudo-dipeptides products also can be used to protect cosmetic oils easily oxidizable, rich in unsaturated fatty acids formulated in cosmetic or dietetic.

It has been necessary to add 15 to 25 mmol of pseudo-dipeptides products of the invention per liter of oil according to the following formulation:

20 mmol of acetylated b-alanyl-histamine oil extracted from micro seaweed cultured in sea water very rich in unsaturated fatty acids, including EPA qs for 1L.

We have compared the ageing of this protected oil to the non-protected oil at the end of a month by the malondialdehyde dosage. For the non-protected oil, we observe an important increase of dialdehyde content, which proves well the activity of the acetylated-β-alanyl-histamine in the protection against oxidation.

EXAMPLE 10

According to the same principle as previously we have prepared the following cosmetic oil:

25 mmol of 8-amino-octanoyl-histamine rosa mosqueta oil qs for 1L

We have compared the products protected oil/non-protected oil at the end of 5 weeks by acid tritation. The dosage of this latter in this case presents a significant increase (value above to 10 for the non-protected oil). Therefore, we can conclude that the presence of 8-amino-octanoyl-histamine has an antioxidant action on rosa mosqueta oil.

All the above examples have shown that the pseudo-dipeptides according to the invention are active in a statistical range of 1 to 100 millimoles of active per litter with a main peak of activity between 10 to 25 mM.

Although the present invention has been described in relation to particular embodiments thereof, many other variations and modifications and other uses will become apparent to those skilled in the art. Therefore, the present invention is limited not by the specific disclosure herein, but only by the appended claims.

What is claimed is:

1. A composition comprising an effective amount of an active ingredient and a carrier therefor, wherein said active ingredient is an anti-oxidant, cytostimulant or immunomodulant, containing a pseudo-dipeptide product which is histamine or methyl-substituted histamine coupled to an amino-acid of the formula:

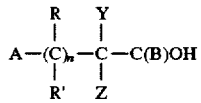

in which A is an amine, amide, lactam or urethane radical; each R and R' in each repeating unit individually represents hydrogen, a hydrocarbon radical, or a functional group selected from the group consisting of hydroxy, carboxy, thiol, amine, alkoxy, thioether, sulphate and phosphate; Y and Z each represent hydrogen, fluorine or a hydrocarbon radical substituted by at least one said functional group. B is O or S and n is an integer above or equal to 1, the covalent bond with histamine or methyl-substituted histamine being a peptidic bond between the acid radical of the amino acid and the amine radical of histamine.

2. The composition according to claim 1 characterized in that B is O.

3. The composition according to claim 2 characterized in that A is

in which X is hydrogen or acetyl.

4. The composition according to claim 3 characterized in that the amino-acid has as a formula:

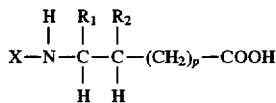

in which $R_1$ is hydrogen or phenyl, $R_2$ is hydrogen or methyl, and p is 0, 1, 2 or 3.

5. The composition according to claim 3 characterized in that said amino acid is selected from the group consisting of β-alanine, τ-aminobutyric acid, β-amino-isobutyric acid, 5-aminovaleric acid, 3-phenyl-3-aminopropionic acid, 6-aminocaproic acid, 8-aminooctanoic acid, N-acetyl-β-alanine, N-acetyl-3-phenyl-3-aminopropionic acid, 4-methyl-aminobutyric acid, DL-β-aminobutyric acid and L-glutamic acid.

6. The composition according to claim 3 which is β-alanyl-histamine.

7. The composition according to claim 1 characterized in that B is S.

8. The composition according to claim 2 in the form of a medication.

9. The composition according to claim 8, in the form of an eye-care formulation.

10. The composition according to claim 8, comprising an injectable containing β-alanyl-histamine.

11. The composition according to claim 8, in which the active ingredient is an anti-oxidant.

12. The composition according to claim 11 in the form of a medicine containing an atherosclerosis treatment effective amount of active ingredient.

13. The composition according to claim 11 in the form of a medicine containing a cataract treatment effective amount of active ingredient.

14. The composition according to claim 11 in the form of a medicine containing a radioprotective effective amount of active ingredient.

15. The composition according to claim 8, in which the active ingredient is a cytostimulant.

16. The composition according to claim 15 in the form of a medicine containing a tissue regeneration effective amount of active ingredient.

17. The composition according to claim 8, in which the active ingredient is an immunomodulant.

18. The composition according to claim 17 in the form of a medicine containing an allergy blocking effective amount of active ingredient.

19. The composition according to claim 8 in the form of a medicine for treatment of oxidative stress.

20. The composition according to claim 8 in the form of a topical medicine.

21. The composition according to claim 8, adapted for the treatment of dry eye, comprising:

phosphatidylcholine liposomes . . . about 8 mg/ml fibronectin of human plasma origin . . . about 10 μg/ml and β-alanyl-histamine . . . about 25 μg/ml.

22. The composition according to claim 2 containing a material sensitive to oxidation, or an organ or tissue preserved ex vivo.

23. The composition according to claim 2 in the form of a cosmetic.

24. A method of administering to a host in need of an antioxidant cytostimulant or immunomodulant treatment an effective amount of an active ingredient which is a pseudo-dipeptide product which is histamine or methyl-substituted histamine coupled to an amino-acid of the formula:

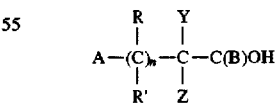

in which A is an amine, amide, lactam or urethane radical; each R and R' in each repeating unit individually represents hydrogen, a hydrocarbon radical, or a functional group selected from the group consisting of hydroxy, carboxy, thiol, amine, alkoxy, thioether, sulphate and phosphate; Y and Z each represent hydrogen, fluorine or a hydrocarbon radical substituted by at least one said functional group. B is O or S and n is an integer above or equal to 1, the covalent bond with histamine or methyl-substituted histamine being a peptidic bond between the acid radical of the amino acid and the amine radical of histamine.

25. The method according to claim 24 characterized in that B is O.

26. The method according to claim 25 characterized in that A is

in which X is hydrogen or acetyl.

27. The method according to claim 26 characterized in that the amino-acid has as a formula:

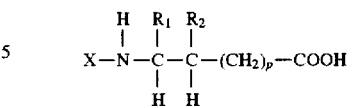

in which $R_1$ is hydrogen or phenyl, $R_2$ is hydrogen or methyl, and p is 0, 1, 2 or 3.

28. The method according to claim 24 characterized in that B is S.

* * * * *